US006407089B1

(12) United States Patent
Johnson

(10) Patent No.: US 6,407,089 B1
(45) Date of Patent: Jun. 18, 2002

(54) TRIAZATRINAPHTHYRINS AND THE USE THEREOF

(75) Inventor: Martin R. Johnson, Piedmont, CA (US)

(73) Assignee: Trinapco Inc., San Leandro, CA (US)

( * ) Notice: Subject to any disclaimer, the term of this patent is extended or adjusted under 35 U.S.C. 154(b) by 15 days.

(21) Appl. No.: 09/742,293

(22) Filed: Dec. 22, 2000

Related U.S. Application Data

(60) Provisional application No. 60/171,583, filed on Dec. 23, 1999.

(51) Int. Cl.[7] ..................... A61K 31/555; C07D 225/00
(52) U.S. Cl. ..................... 514/183; 514/185; 514/279; 540/465; 540/472
(58) Field of Search ................................. 540/465, 472; 514/183, 185, 279

(56) References Cited

U.S. PATENT DOCUMENTS

| 4,169,092 A | 9/1979 | Bayer ........................... 546/10 |
| 5,645,818 A | 7/1997 | Jackels et al. ........... 424/9.363 |
| 5,925,744 A | 7/1999 | Haner et al. .................. 534/15 |

FOREIGN PATENT DOCUMENTS

| GB | 915950 | 1/1963 |

OTHER PUBLICATIONS

Tsuchiya, T. et al., "Photolysis of Tetrazolo[1,5–b]pyridazines; Formation of Cyclopropenes," *J. Chem. Soc., Chem. Commun.* 19:1059–60 (1972).

Groth, P., "Crystal Structure of a Cyclisation Product of 6–Chloropyrid–2–thione $(C_{15}H_9N_3S_3)$," *Acta Chem. Scand.*, 27(1):5–14 (1973).

Newkome, G.R., et al., "Chemistry of Heterocyclic Compounds. 61. Synthesis and Conformational Studies of Macrocycles Possessing 1,8– or 1,5–Naphthyridino Subunits Connected by Carbon–Oxygen Bridges," *J. Org. Chem.* 46(5):833–839 (1981).

Chandler, C.J., et al., "The Synthesis of Macrocyclic Polyether–Diesters Incorporating 1,10–Phenanthrolino and 1,8–Naphthyridino Subunits," *J. Heterocyclic Chem.* 19:1017–1019 (1982).

Johnson, M. "Hexaform Macrocyclic Ligands," Programs and Abstracts, XXth International Symposium on Macrocyclic Chemistry, Jerusalem, Israel, Jul. 2–7, 1995.

Bergman, J., et al., "Powder Diffraction Investigations on Molecular Crystals of the Ring System Cyclo–Tri(2,6–Pyridyl Formamidine)," *Materials Science Forum* 228–231:869–872 (1996).

*Primary Examiner*—Mukund J. Shah
*Assistant Examiner*—Tamthom N. Truong
(74) *Attorney, Agent, or Firm*—Stern, Kessler, Goldstein & Fox P.L.L.C.

(57) ABSTRACT

A novel class of macrocycles, termed triazatrinaphthyrins, is disclosed having general Formula I:

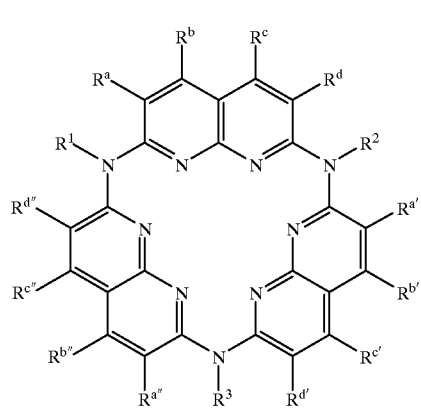

Figure 1:
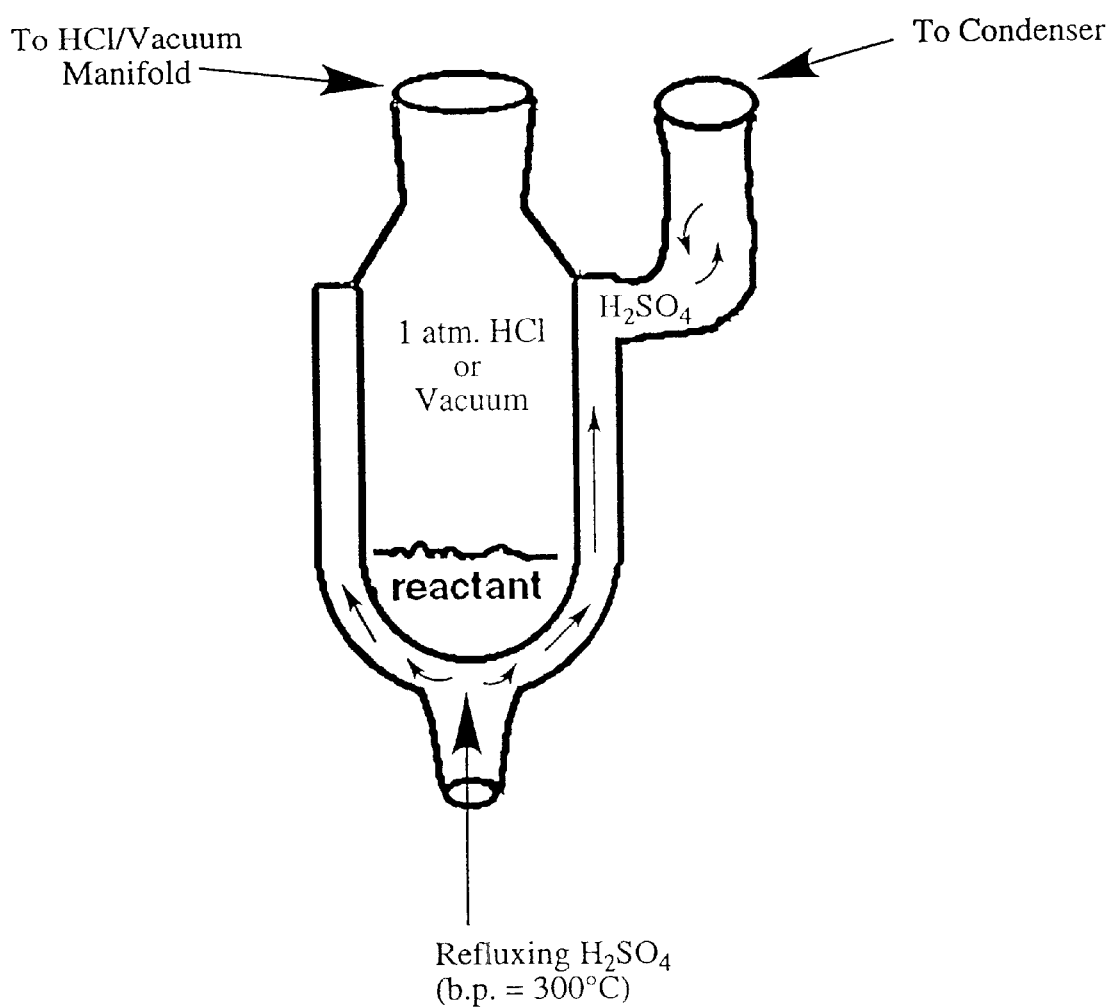

or a solvate, hydrate, ester or salt thereof; wherein $R^1$, $R^2$, $R^3$, $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are defined in the specification. The macrocycles are useful in the extraction of transition metals, in particular in the extraction of lanthanides.

12 Claims, 1 Drawing Sheet

TRIAZATRINAPHTHYRINS AND THE USE THEREOF

CROSS-REFERENCE TO RELATED APPLICATIONS

This application claims benefit under 35 U.S.C. §119(e) of U.S. Provisional Application No. 60/171,583, filed Dec. 23, 1999.

STATEMENT REGARDING FEDERALLY-SPONSORED RESEARCH AND DEVELOPMENT

Not applicable.

REFERENCE TO MICROFICHE APPENDIX/SEQUENCE LISTING/TABLE/COMPUTER PROGRAM LISTING APPENDIX (submitted on a compact disc and an incorporation-by-reference of the material on the compact disc)

Not applicable.

BACKGROUND OF THE INVENTION

1. Field of the Invention

The present invention relates to macrocycles having three naphthyridine subunits and salts and metal complexes thereof; to a process for the preparation of these macrocycles, their salts and complexes; and to the use of compositions of these macrocycles for extracting a transition metal and a method for extracting a transition metal using the composition.

2. Background Art

The transition metals include the nine metals of Group VIII of the periodic table, as representative examples thereof, and the lanthanide and actinide metals. The transition metals further include the metals called rare metals, noble metals, and heavy metals. Specific examples thereof include iron (Fe), cobalt (Co), nickel (Ni), ruthenium (Ru), rhodium (Rh), palladium (Pd), osmium (Os), iridium (Ir), platinum (Pt), titanium (Ti), vanadium (V), chromium (Cr), manganese (Mn), copper (Cu), zinc (Zn), yttrium (Y), zirconium (Zr), niobium (Nb), molybdenum (Mo), silver (Ag), cadmium (Cd), lanthanum (La), cerium (Ca), neodymium (Nd), samarium (Sm), europium (Eu), gadolinium (Gd), terbium (Tb), holmium (Ho), erbium (Er), thulium (Tm), ytterbium (Yb), lutetium (Lu), hafnium (Hf), tantalum (Ta), tungsten (W), gold (Au), mercury (Hg), uranium (U), and plutonium (Pu). These transition metals are used not only in catalysts and iron/steels but also in a wide variety of other applications such as hydrogen-absorbing alloys, batteries, magnets, and superconductive materials. These metals are desired to be recovered from so-called secondary resources from the standpoint of stable supply. Furthermore, it in necessary to treat industrial drainage and the like to remove the metals contained therein in slight amounts. Thus, the establishment of an efficient metal recovery technique is an important subject also from the standpoint of environmental protection.

One of the elemental techniques for the recovery and purification of transition metals is the solvent extraction method. The solvent extraction method has conventionally employed an acid, basic, or neutral extracting agent according to the composition of the solution to be treated. Besides being used alone, transition metals have recently come to be used as composites and similar materials such as alloys and mixtures. It is hence thought that the solvent extraction method comes to be utilized increasingly.

There is a desire for an extracting agent which has higher extraction capacity, higher extraction rate, and higher selectivity and is harmless and inexpensive.

BRIEF SUMMARY OF THE INVENTION

An object of the present invention is to provide an extracting agent for a transition metal which has a novel structure entirely different from the structure of any known extracting agent for a transition metal and has excellent extracting performance.

Another object of the present invention is to provide a method for extracting a transition metal with the extracting agent.

The present invention addresses these and other shortcomings in the prior art by providing macrocyclic compounds for use in specific metal ion binding. The invention concerns a class of novel macrocycles, termed triazatrinaphthyrins, and their metal complexes and salts. In a general and overall sense, the novel triazatrinaphthyrin compounds of the present invention include those with structures in accordance with general Formula I:

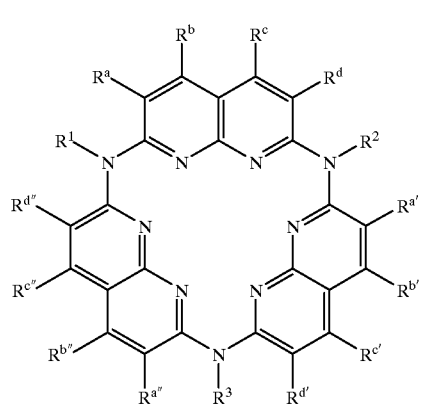

or a solvate, hydrate, ester or salt thereof; wherein $R^1$–$R^3$ and $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are as defined below.

These and other objects of the present invention are accomplished by a composition for extracting a transition metal which comprises as an active ingredient a triazatrinaphthyrin or a salt thereof.

Furthermore, these and other objects of the present invention are accomplished by a method for extracting a transition metal which comprises extracting a transition metal with the above-described composition for extracting a transition metal.

BRIEF DESCRIPTION OF THE DRAWINGS/FIGURES

FIG. 1 depicts a vertical Abderhalden apparatus for use in the synthesis of the triazatrinaphthyrin macrocycles of the present invention.

DETAILED DESCRIPTION OF THE INVENTION

The novel triazatrinaphthyrin compounds of the present invention include those with structures in accordance with general Formula I:

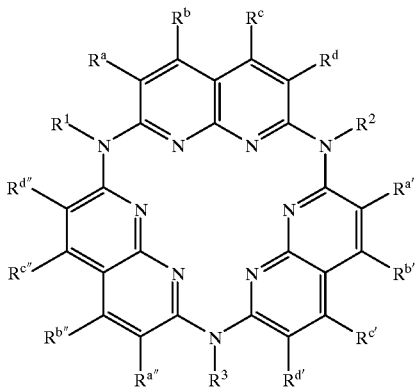

or a solvate, hydrate, ester or salt thereof; wherein:

$R^1$, $R^2$ and $R^3$ are each independently selected from hydrogen, alkyl, cycloalkyl, aryl, aralkyl, heterocycle and formyl, any of which is optionally substituted;

$R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each independently selected from hydrogen, alkyl, cycloalkyl, hydroxyalkyl, alkoxyalkyl, aryloxyalkyl, alkenyl, alkynyl, aryl, acyl, heterocycloalkyl, sulfonyl, alkylsulfonyl, arylsulfonyl, aminosulfonyl, nitroalkyl, aminoalkyl, monoalkylaminoalkyl, dialkylaminoalkyl, carboxy, amino, nitro, cyano, acyl, aminocarbonyl, hydroxy, alkoxy, aryloxy, aminocarbonyloxy, carbonylamino, sulfonylamino or aralkyl, any of which is optionally substituted.

When a group is optionally substituted, the optional substituents can be one or more non-hydrogen substituents, provided that the resulting compound is stable. Values of optional substituents are halogen, hydroxy, alkyl, cycloalkyl, aralkyl, aryl, thiol, amino, monoalkylamino, dialkylamino, formylamino, aminoiminomethyl, acylamino, aminoacyl, mono- or di-alkylaminocarbonyl, thiocarbonylamino, thioacylamino, aminothiocarbonyl, alkoxy, aryloxy, aminocarbonyloxy, mono- or di-alkylaminocarbonyloxy, mono- or diarylaminocarbonyloxy, mono- or diaralkylaminocarbonyloxy, alkylsulfonyl, arylsulfonyl, aralkylsulfonyl, alkylsulfonylamino, arylsulfonylamino, aralkylsulfonylamino, alkoxycarbonylamino, aralkoxycarbonylamino, aryloxycarbonylamino, mono- or di-alkylaminothiocarbonyl, aralkoxy, carboxy, carboxyalkyl, alkoxycarbonyl, alkoxycarbonylalkyl, nitro, cyano, trifluoromethyl, alkylthio and arylthio.

Preferred values of optional substituents on alkyl and cycloalkyl groups are chloro, hydroxy, amino, mono($C_{1-4}$) alkylamino, di($C_{1-4}$)alkylainino, formylamino, $C_{2-6}$ acylamino, aminocarbonyl, $C_{2-8}$ aminoacyl, $C_{1-6}$ alkoxy, $C_{6-14}$ aryloxy, carboxy, carboxy($C_{1-6}$)alkyl, $C_{2-8}$ alkoxycarbonyl, nitro, cyano, trifluoromethyl, $C_{1-6}$ alkylthio, $C_{6-4}$ arylthio, $C_{1-6}$ alkylsulfonylamino, $C_{7-15}$ aralkylsulfonylamino, $C_{6-10}$ arylsulfonylamino, mono- or di($C_{1-6}$)alkylaminocarbonyloxy, mono- or di-($C_{6-10}$) arylaminocarbonyloxy, mono- or di($C_{7-15}$) aralkylcarbonyloxy, $C_{1-6}$ alkoxycarbonylamino, $C_7$–$C_{15}$ aralkoxycarbonylamino, and $C_6$–$C_{10}$ aryloxycarbonylamino.

Preferred values of optional substituents on aryl-containing and heterocyclic-containing groups include chloro, hydroxy, amino, mono($C_{1-4}$) alkylamino, di($C_{1-4}$) alkylamino, formylamino, $C_{2-6}$ acylamino, aminocarbonyl, $C_{2-8}$ aminoacyl, $C_{3-7}$ cycloalkyl, $C_{1-6}$ alkyl, $C_{1-6}$ alkoxy, $C_{6-14}$ aryloxy, carboxy, carboxy($C_{1-6}$)alkyl, $C_{2-8}$ alkoxycarbonyl, nitro, cyano, trifluoromethyl, $C_{1-6}$ alkylthio, $C_{6-14}$ arylthio, $C_{6-14}$ aryl, phenyl (further optionally substituted by one, two or three of chloro, hydroxy, $C_{1-4}$ alkyl, $C_{1-4}$ alkoxy, amino or carboxy), tetrazolyl (further optionally substituted by one, two or three of chloro, hydroxy, $C_{1-4}$ alkyl, $C_{1-4}$ alkoxy, amino or carboxy), thienyl (further optionally substituted by one, two or three of chloro, hydroxy, $C_{1-4}$ alkyl, $C_{1-4}$ alkoxy, amino or carboxy), 3,4-methylenedioxy, 3,4-ethylenedioxy, 3,4-propylenedioxy, $C_{1-6}$ alkylsulfonylamino, $C_{7-5}$ aralkylsulfonylamino, $C_{1-6}$ arylsulfonylamino, $C_{1-6}$ alkylsulfonyl, $C_{6-10}$ arylsulfonyl, mono- or di($C_{1-6}$)alkylaminocarbonyloxy, mono-or di-$C_{6-10}$ arylaminocarbonyloxy, mono- or di-($C_{7-15}$) aralkylcarbonyloxy, $C_{1-6}$ alkoxycarbonylamino, $C_7$–$C_{15}$ aralkoxycarbonylamino, $C_6$–$C_{10}$ aryloxycarbonylamino, $C_{2-6}$ thioacylamino, aminothiocarbonyl, and $C_{2-8}$ amnothioacyl.

Preferred values of $R^1$, $R^2$ and $R^3$ are hydrogen.

Preferred values of $R^b$, $R^{b'}$, $R^{b''}$, $R^c$, $R^{c'}$ $R^{c''}$ are hydrogen, $C_{1-6}$alkyl, $C_{3-8}$ cycloalkyl, sulfonyl, and $C_{6-14}$ aryl, any of which is optionally substituted.

Preferred values of $R^a$, $R^{a'}$, $R^{a''}$, $R^d$, $R^{d'}$ and $R^{d''}$ are hydrogen, $C_{1-6}$ alkyl, sulfonyl and $C_{6-14}$ar($C_{1-6}$)alkyl, any of which is optionally substituted.

Methods for the preparation of various 3-, 4-, 5- and 6-substituted naphthyridines as starting materials for the preparation of the correspondingly substituted triazatrinaphthyrins are described herein. Functional group manipulation of the 3-, 4-, 5- and 6-positions ($R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$) is possible after macrocycle formation, or the appropriately substituted naphthyridines may be used directly, depending upon the particular triazatrinaphthyrin desired.

Triazatrinaphthyrin itself (wherein $R^1$–$R^3$ and $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each hydrogen) is a macrocycle which is generally characterized by the presence of three 2-amino-1,8-naphthyridine subunits contained within a macrocyclic framework and by emission bands that are red shifted as compared to those of porphyrins.

Triazatrinaphthyrin and its substituted derivatives are characterized by the ability to form complexes with metal ions.

Triazatrinaphthyrin and its substituted derivatives are further characterized by the ability to undergo facile protonation at one or more naphthyridine nitrogens and/or bridging "meso" nitrogens. It is understood that the triazatrinaphthyrin compounds of the present invention may be either singly or doubly protonated, and in certain embodiments triply or four-fold protonated.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, wherein there is at least one double bond between two of the carbon atoms in the chain including, but not limited to, ethenyl, 1-propenyl, 2-propenyl, 2-methyl-1-propenyl, 1-butenyl, 2-butenyl, and the like.

Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkylthio" as employed herein by itself or as part of another group refers to a straight or branched chain radical of 1 to 20 carbon atoms, bonded to a sulfur atom, including, but not limited to, methylthio, ethylthio, n-propylthio, isopropylthio, and the like. Preferably the alkylthio chain is 1 to 10 carbon atoms in length, more preferably 1 to 8 carbon atoms in length.

The term "alkoxy" as employed herein by itself or as part of another group refers to a straight or branched chain radical of 1 to 20 carbon atoms, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "halogen" or "halo" as employed herein by itself or as part of another group refers to chlorine, bromine, fluorine or iodine with chlorine being preferred.

The term "acyl" as employed herein by itself or as part of another group refers to the group —C(O)R$^g$ where R$^g$ is alkyl, alkenyl, alkynyl, aryl, aralkyl, aralkenyl, heteroaryl, heteroarylalkyl or heteroarylalkenyl. Preferred acyl groups are alkanoyl, aralkanoyl and aroyl groups (—C(O)R$^g$ where R$^g$ is $C_{1-8}$ alkyl, $C_{6-10}$ aryl($C_{1-4}$)alkyl or $C_{6-10}$ aryl).

The term "thioacyl" as employed herein by itself or as part of another group refers to the group —C(S)R$^g$ where R$^g$ is alkyl, alkenyl, alkynyl, aryl, aralkyl, aralkenyl, heteroaryl, heteroarylalkyl or heteroarylalkenyl, preferably $C_{1-8}$ alkyl.

The term "thiocarbonyl" as employed herein by itself or as part of another group refers to the group —C(S)—.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl or tetrahydronaphthyl.

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The terms "heterocyclic," "heterocyclo" or "heterocycle" as employed herein by themselves or as part of larger groups refers to a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be, optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, indanyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an NR$^y$R$^z$ moiety, wherein R$^y$ and R$^z$ are, independently from one another, hydrogen or $C_{1\,to\,C8}$ alkyl, or together with the nitrogen to which they are bound, form a saturated or unsaturated 5-, 6-, or 7-membered ring.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2, 3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "substituted", as used herein, means that one or more hydrogens of the designated moiety are replaced with a selection from the indicated group, provided that no atom's normal valency is exceeded, and that the substitution results in a stable compound. When a substituent is keto (i.e., =O), then 2 hydrogens attached to an atom of the moiety are replaced.

By "stable compound" or "stable formula" is meant herein a compound that is sufficiently robust to survive isolation to a useful degree of purity from a reaction mixture and formulation into an efficacious therapeutic or diagnostic agent.

The triazatrinaphthyrin macrocycles of the present invention may be protonated and exist in the form of a salt. The terms "salt", "acid addition salt" or "pharmaceutically acceptable salt" are intended to include all acceptable salts. Examples of acid salts are hydrochloric, hydrobromic, hydrofluoric, perchloric, nitric, sulfuric, phosphoric, formic, acetic, trifluoroacetic, propionic, maleic, succinic, malonic, methane sulfonic and the like. A triazatrinaphthyrin macrocycle of the present invention in the form of a salt is characterized by the pronation of one of more nitrogen atoms. The complete salt consists of the monoprotonated or multiprotonated macrocycle and its associated anion(s).

Macrocycle Synthesis

The preferred starting material for the preparation of the triazatrinaphthyrin macrocycles of the present invention is the appropriately substituted 2,7-diamino-1,8-naphthyridine.

Scheme 1 illustrates the synthetic sequence for the preparation of various 2,7-diamino-1,8-naphthyridines (5a). As shown, this is accomplished by reacting the corresponding 2-amino-7-chloro-1,8-naphthyridine (4) or 2,7-dichloro-1,8-naphthyridine (7) with anhydrous ammonia or other amine. The 2-amino-7-chloro-1,8-naphthyridines (4) can be prepared according to the method of Carboni, S. et al., *Gazz. Chim. Ital.* 96(11):1456–1459 (1966), herein incorporated by reference in its entirety, which begins with the formation of 2-amino-7-hydroxy-1,8-naphthyridine (3) from the appropriately substituted 2,6-diaminopyridine (1) and $\mu$-ketoester (2). Those of skill in the art of organic synthesis will appreciate the availability of alternate reagents and conditions for affecting the conversions outlined in Scheme 1.

Scheme 1

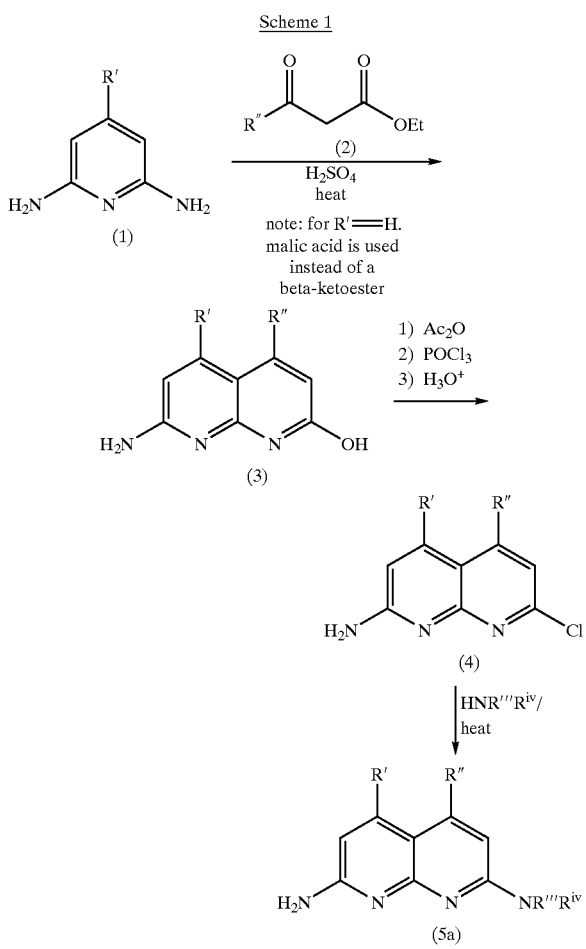

2,7-diamino-1,8-naphthyridines ((5a), R'''=R$^{iv}$=H) may be functionalized to provide the desired $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ groups of Formula I. For example, as shown in Scheme 2 below, protection of the 2- and 7-amino groups with a suitable protecting group and subsequent treatment with base generates one or more nucleophilic carbon atoms on the naphthyridine ring which can react with the appropriate electrophile (e.g., alkyl halides, epoxides, anhydrides, sulfonate esters and the like) to arrive at a functionalized 2,7-diaminonaphthyridine for use in the subsequent macrocycle forming reaction.

Scheme 2

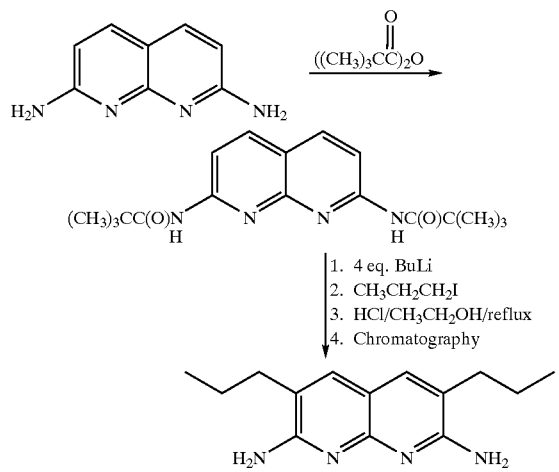

For certain $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ substituents of Formula I which are incompatible with the reaction conditions of macrocycle formation, and which cannot be prepared by derivatization of other groups, functional group manipulation of those positions may be carried out after macrocycle formation.

The synthetic strategies outlined herein allow for the formation of triazatrinaphthyrins wherein $R^a$, $R^{a'}$, $R^{a''}$, $R^d$, $R^{d'}$ and $R^{d''}$ of Formula I are hydrogen, alkyl, hydroxyalkyl, alkoxyalkyl, aryloxyalkyl, alkenyl, alkynyl, acyl, heterocycloalkyl, alkylsulfonyl, arylsulfonyl, nitroalkyl, aminoalkyl, monoalkylamainoalkyl, dialkylaminoalkyl or aralkyl, any of which is optionally substituted; and $R^b$, $R^{b'}$, $R^{b''}$, $R^c$, $R^{c'}$ and $R^{c''}$ of Formula I are each independently selected from hydrogen, alkyl, cycloalkyl, alkenyl, alkynyl, aryl, aralkyl, carboxy, amino, nitro, cyano, acyl, aminocarbonyl, alkylsulfonyl, arylsulfonyl, aminosulfonyl, hydroxy, alkoxy, aryloxy, aminocarbonyloxy, carbonylamino, sulfonylamino, any of which is optionally substituted.

Scheme 3 illustrates the synthesis of the parent triazatrinaphthyrin (wherein $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ of Formula I are each hydrogen). The macrocycle forming reaction is carried out in a vertical Abderhalden apparatus (see FIG. 1) or in a tube furnace, the latter providing better temperature control. In general, the macrocycle forming reaction is characterized by the treatment of a 2,7-diamino-1,8-naphthyridine with hydrogen halide gas at a temperature sufficient to cause melting of the 2,7-diamino-1,8-naphthyridine in 1 atmosphere of hydrogen halide gas. While not intending to be limited to any mechanistic explanation, the reaction is believed to proceed by elevation of a hydrohalide salt of 2,7-diamino-1,8-naphthyridine to a temperature sufficient to cause amine extrusion and triazatrinaphthyrin formation. The details of an embodiment of the synthesis as carried out in the Abderhalden apparatus are outline in Example 1.

It is to be understood that the macrocycle-forming reaction can be carried out with a single 2,7-diamino-1,8-naphthyridine or with a mixture of 2,7-diamino-1,8- naphthyridines. When the macrocycle-forming reaction is carried out with a mixture of 2,7-diamino-1,8-naphthyridines, a mixture of products (including various regioisomers) is obtained. One of skill in the art will appreciate various chromatographic media and solvent systems capable of separating a mixture of triazatrinaphthyrins and isolating the desired compound from the mixture. Typical chromatographic media include various mesh sizes of silica gel or alumina and typical solvent systems include mixtures of polar and non-polar solvents such as $CHCl_3$/$CH_3OH$, $CH_2Cl_2$/$CH_3OH$, and others known in the art of chromatography.

An alternative embodiment of the process for forming triazatrinaphthyrins involves the use of a hydrohalide salt of an aromatic amine or a mixture of aromatic amines (including, but not limited to, pyridinium hydrochloride, quinoline hydrochloride or 4-(3-phenylpropyl)pyridine hydrochloride) as a solvent in which a 2,7-diamino-1,8-naphthyridine is dissolved and the temperature elevated sufficiently to cause melting of the solvent and amine extrusion and triazatrinaphthyrin formation. Certain solvents, such as pyridinium hydrochloride, when heated to near its boiling point of 222° C., facilitate the formation of triazatrinapthyrin in 1 atmosphere of hydrogen chloride at temperatures well below 300° C.

At sufficiently elevated temperatures, the use of hydrogen chloride or a hydrohalide salt may not be necessary to effect formation of the triazatrinapthyrin. Specifically, the di-n-propyl-diarinonaphthyriine outlined in Scheme 2, when heated rapidly and briefly to its melting point of about 340° C. in a sealed tube, spontaneously forms the corresponding hexapropyl triazatrinapthyrin in good yield. Accordingly, the present invention also encompasses a process for forming a triazatrinaphthyrin by heating a 2,7-diamino-1,8-naphthyridine at, or above, its melting temperature to yield the desired triazatrinaphthyrin.

include paramagnetic ions of elements such as Gd, In, Eu, Dy, Pr, Pa, Cr, Co, Fe, Cu, Ni, Ti, and V, preferably Gd or Eu. Complex formation is typically carried out in a polar solvent, including but not limited to, water, isopropanol, ethanol, methanol, acetone, DMF, DMSO, acetonitrile and the like. Solvent systems including a mixture of solvents and/or aqueous solvent mixtures are also contemplated. Typically, the metal ion in the form of its halide or acetate salt is used in the complex forming reaction. An exemplary complex forming reaction is described in Example 2.

Protonated Macrocycles

Triazatrinaphthyrins undergo facile protonation at one or more naphthyridine nitrogens or at one or more apical (or "meso") nitrogens. Typically, a triazatrinaphthyrin is contacted with an acid selected from hydrochloric, hydrobromic, hydrofluoric, perchloric, nitric, sulfuric, phosphoric, formic, acetic, trifluoroacetic, propionic, maleic, succinic, malonic, and methane sulfonic in an aqueous solution. The resulting singly or multi-protonated macrocycle is associated with one or more negatively charged counterions, depending on the acid used to protonate the macrocycle.

EXAMPLE 1

11,22,33-Triazatrinaphthyrin a. 2,7-Diamino-1,8-naphthyridine. 2-Amino-7-chloro-1, 8-naphthyridine (50 grams, 0.28 moles), prepared by the method of Carboni, S. et al., *Gazz. Chim. Ital.* 96(11): 1456–1459 (1966), was loaded into a 2 liter Parr bomb and charged with liquid anhydrous ammonia (500 ml). The bomb was sealed, brought to a pressure of 1200 PSI, and maintained at this pressure for 14 hours. The bomb was then cooled to room temperature, the ammonia vented, and the bomb contents extracted, first with 1.5 liters of saturated

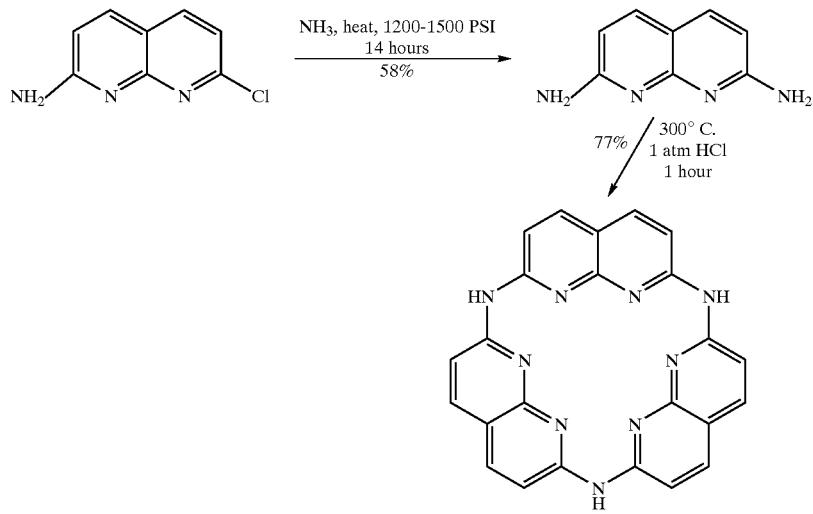

Scheme 3

Metalation/Addition of Radioisotopes

The triazatrinaphthyrin compounds of the present invention include those where the triazatrinaphthyrin is complexed with certain metals for use as a transition metal complexing agent, or simply as a convenient form of the compound. Examples of metals which are appropriate aqueous ammonia, then with 500 ml of saturated aqueous ammonia. These clear yellow liquid extracts were combined and concentrated on the rotary evaporator to a volume of about 250 ml, yielding a flocculent precipitate which was collected and dried to give the product 2,7-diamino-1,8-naphthyridine (26 g, 162 mmol, 58%), mp 311° C. (lit.

mp=222–223° C.; Collin, J. P., et al., *Inorg Chim. Acta* 201:29–34 (1992)). $^1$H NMR (DMSO-d$_6$): δ 7.76 (d, J=9 Hz, 2H, CH), 71.4 (br.s., 4H, NH$_2$), 6.50 (d, J=9 Hz, CH). $^{13}$C NMR: δ 160.7, 144.4, 140.2, 109.9, 108.6. MS m/e 160 (100%), 133 (25%), 105 (9%). HRMS calc'd for C$_8$H$_8$N$_4$: m/e=160.074896. Found: m/e=160.074984. UV-visible λ$_{max}$ (log e) (25% aqueous EtOH): 352(4.07). Emission λ$_{max}$ (arbitrary units) (25% aq. EtOH/IPA):, 407(0.48), 493(1.00).

b. 11,22,33-Triazatrinaphthyrin. A custom-built vertical Aberhalden apparatus (see FIG. 1) was charged with 2,7-diamino-1,8-naphthyridine (12 grams) and capped with a stoppered top leading to a manifold capable of replacing a vacuum with 1 atmosphere of anhydrous hydrogen chloride gas. The diaminonaphthyridine was held under vacuum in the inner chamber of the Aberhalden vessel until such time as condensing vapors of sulfuric acid (bp=300° C.) began to bathe the outside of the inner chamber and the diaminonaphthyridine began to change color from the heat. The vacuum was then promptly replaced with 1 atm of anhydrous hydrogen chloride. The diaminonaphthyridine quickly melted, darkened, and began to bubble. After 40 minutes the darkened reaction mass had completely resolidified, and heating was continued for an additional 20 minutes. The apparatus was allowed to cool, and the crude product was removed from the vessel and ground to a powder. This whole process was repeated and the two batches were combined and washed as follows: The dark powder was stirred with 200 ml concentrated aqueous ammonia for 30 minutes, then filtered, and the moist solid so obtained was washed two more times by stirring for 1 hour with 500 ml warm ethanol saturated with ammonia vapor. The remaining solid material (dry weight 19 grams) was stirred for 12 hours in 250 ml of glacial acetic acid held at 60 ° C. The resultant dark solution was filtered through a medium glass fritted funnel and concentrated to dryness on a rotary evaporator. The residue so obtained was dried in vacuo at 100° C. for 24 h to give the product as a dark purple solid (16.5 g, 38.5 mmole, 77%). $^1$H NMR (CF$_3$COOD): δ 7.98 (d, J=9.3 Hz, 2H, CH), 6.95 (d, J=9.3 Hz, CH). $^{13}$C NMR (CF$_3$COOD): δ 155.5, 144.8, 144.3, 118.1, 116.3. MS m/e 429 (100%), 214 (10%). HRMS calc'd for C$_{24}$H$_{15}$N$_9$: m/e=429.1450. Found: me=429.1449. UV-visible λ$_{max}$ (log e) (HOAc): 340 (4.78), 356 (4.96), 406 (3.51), 480–82sh (3.11). Emission λ$_{max}$ (arbitrary units)(sh=shoulder) (concentrated HCl): 535–542sh (0.275), 569 (1.00), 615 (0.29).

EXAMPLE 2

11,22,33-Triazatrinaphthyrin a Gd(III) Acetate

A 50 mL flask is charged with 11,22,33-triazatrinaphthyrin (100 mg, 0.23 mol) and 15 mL 33% aqueous acetic acid. The clear dark solution is stirred at room temperature and Gd(III) chloride hexahydrate (75 mg, 0.20 mol) in 2 mL of water is added in one portion. Complex formation may monitored by observing the characteristic changes in UV-Vis absorption, although complex formation is essentially complete within a minute. The resulting solution is evaporated under reduced pressure and washed with glacial acetic acid to remove uncomplexed triazatrinaphthyrin. The resulting complex is obtained in quantitative yield based on the amount of staring Gd(III) chloride hexahydrate.

Extraction of Metals

Besides the nine elements of Group VIII of the periodic table, the transition metals include the elements of Groups 3A to 7A and Groups 1B and 2B, that is, the elements ranging from scandium, having an atomic number of 21, to zinc, having an atomic number of 30, from yttrium, having an atomic number of 39, to cadmium, having an atomic number of 48, from lanthanum, having an atomic number of 57, to mercury, having an atomic number of 80, and from actinium, having an atomic number of 89, to lawrencium, having an atomic number of 103. Specifically, the transition metals include the elements of Group VIII, i.e., iron (Fe), cobalt (Co), nickel (Ni), ruthenium (Ru), rhodium (Rh), palladium (Pd), osmium (Os), iridium (Ir), and platinum (Pt), and further include titanium (Ti), vanadium (V), chromium (Cr), manganese (Mn), copper (Cu), zinc (Zn), yttrium (Y), zirconium (Zr), niobium (Nb), molybdenum (Mo), silver (Ag), cadmium (Cd), lanthanum (La), cerium (Ce), neodymium (Nd), samarium (Sm), europium (Eu), gadolinium (Gd), terbium (Tb), holmium (Ho), erbium (Er), thulium (Tm), ytterbium (Yb), lutetium (Lu), hafnium (Hf), tantalum (Ta), tungsten (W), gold (Au), mercury (Hg), uranium (U), and plutonium (Pu).

The solution to be extracted is not particularly limited in the concentration of transition metals dissolved therein. Even when the solution has a transition metal concentration as low as about $1.0 \times 10^{-5}$ M, it is expected to be sufficiently extracted.

Although the aqueous transition metal solution is not particularly limited in pH, it preferably has a pH below 6. As the pH of the solution is altered, the degree of extraction may tend to decrease. In this case, a longer extraction period is necessary as is known in the art.

The extraction temperature is not particularly limited as long as it is not higher than the boiling point of the solvent used. In general, a temperature around room temperature may be used.

The extraction operation is conducted by bringing a solution of the triazatrinaphthyrin into contact with a solution containing transition metals dissolved therein. This contacting is accomplished by shaking, stirring, etc. Although conditions for shaking or stirring are not particularly limited, vigorous shaking or agitation is more effective in efficient extraction. Shaking may be usually conducted at a frequency of about from 100 to 400 times per minute.

An additive for accelerating the extraction (extraction accelerator) can also be used.

Examples of the extraction accelerator include basic nitrogen-containing heterocyclic compounds and aromatic amino acids. Specific examples thereof include nitrogen-containing heterocyclic compounds, such as pyridine, alkylpyridinas (e.g., methylpyridine, ethylpyridine), and quinoline; and amino acids containing an aromatic ring, such an tryptophan and phenylalanine. Examples of the extraction accelerator further include compounds which coordinate to transition metal ions and help the ions to associate with the triazatrinaphthyrin and which thus function to heighten the rate of complex formation with transition metal ions. However, pyridine and tryptophan are preferred.

Although the concentration of the extraction accelerator is not particularly limited, the amount thereof is preferably from 1 to 1,000 gram equivalents per gram equivalent of the transition metal ions to be extracted.

If the amount of the extraction accelerator is too small, the effect of accelerating extraction is not obtained. Conversely, if the amount thereof is too large, there is a fear that the accelerator may alter the properties of the solvent used in an organic phase.

The composition for extracting a transition metal of the present invention is useful for efficiently extracting transition metals, particularly lanthanides, such as gadolinium.

Extraction Example

Extraction of transition metals with a triazatrinaphthyrin of the present invention may be carried out as follows:

In the extraction experiment, 10 ml of an organic phase is prepared by dissolving triazatrinaphthyrin acetate (or other triazatrinaphtyrin macrocycle, salt or complex) in chloroform in a concentration of $5.0 \times 10^{-4}$ M and placing the same in a 30-ml screw vial together with 10 ml of an acetic acid phase containing transition metal chlorides in an amount of $1.0 \times 10^{-4}$ M, and the contents are shaken for 24 hours. In determining the degree of extraction for each metal, the acetic acid phase after the shaking is analyzed with an atomic absorption photometer to determine the concentration of ions of the metal remaining therein. The degree of extraction is calculated using the following equation, wherein $M^+_{total}$ means the initial concentration of the metal ions and $M^+_{solution}$ means the found metal ion concentration in the acetic acid phase after the extraction experiment.

$$\text{Degree of extraction } \% = (M^+_{total} - M^+_{solution})/(M^+_{total} + M^+_{solution})$$

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:
1. A compound of the following Formula:

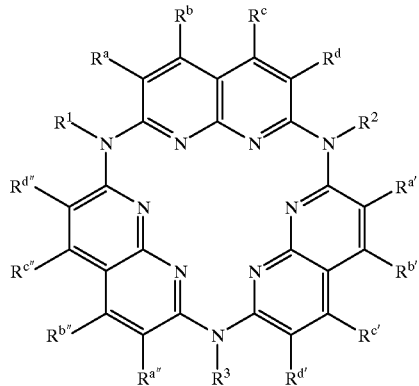

or a solvate, hydrate, ester or salt thereof; wherein:
  $R^1$, $R^2$ and $R^3$ are each independently selected from hydrogen, alkyl, cycloalkyl, aryl, aralkyl, heterocycle and formyl, any of which is optionally substituted;
  $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each independently selected from hydrogen, alkyl, cycloalkyl, hydroxyalkyl, alkoxyalkyl, aryloxyalkyl, alkenyl, alkynyl, aryl, acyl, sulfonyl, alkylsulfonyl, arylsulfonyl, aminosulfonyl, nitroalkyl, aminoalkyl, monoalkylaminoalkyl, dialkylaminoalkyl, carboxy, amino, nitro, cyano, acyl, aminocarbonyl, hydroxy, alkoxy, aryloxy, aminocarbonyloxy, carbonylamino, sulfonylamino or aralkyl, any of which is optionally substituted.

2. A compound of claim 1, wherein $R^1$, $R^2$, $R^3$, $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each hydrogen.

3. A compound of claim 1, wherein said optional substituents are selected from halogen, hydroxy, alkyl, cycloalkyl, aralkyl, aryl, thiol, amino, monoalkylamino, dialkylamino, formylamino, aminoiminomethyl, acylamino, aminoacyl, mono- or di-alkylaminocarbonyl, thiocarbonylamino, thioacylamino, aminothiocarbonyl, alkoxy, aryloxy, aminocarbonyloxy, mono- or di-alkylaminocarbonyloxy, mono- or diarylaminocarbonyloxy, mono- or diaralkylaminocarbonyloxy, alkylsulfonyl, arylsulfonyl, aralkylsulfonyl, alkylsulfonylamino, arylsulfonylamino, aralkylsulfonylamino, alkoxycarbonylamino, aralkoxycarbonylamino, aryloxycarbonylaamino, mono- or di-alkylaminothiocarbonyl, aralkoxy, carboxy, carboxyalkyl, alkoxycarbonyl, alkoxycarbonylalkyl, nitro, cyano, trifluoromethyl, alkylthio and arylthio.

4. A compound of claim 1, in the form of a monoprotonated or multiprotonated acid addition salt, wherein the acid is selected from the group consisting of hydrochloric, hydrobromic, hydrofluoric, perchloric, nitric, sulfuric, phosphoric, formic, acetic, trifluoroacetic, propionic, maleic, succinic, malonic, and methane sulfonic.

5. A singly-protonated or multi-protonated compound of claim 1.

6. A metal complex consisting essentially of a compound of claim 1 and a metal ion.

7. A metal complex of claim 6, wherein said metal is selected from the group consisting of Tc, In, Ga, Gd, Eu, Dy, Pr, Pa, Cr, Co, Fe, Cu, Ni, Ti, and V.

8. A complex according to claim 6, wherein said metal is paramagnetic.

9. A metal complex of claim 8, wherein said metal is Gd(III) or Eu(III).

10. A method of forming a compound of Formula I:

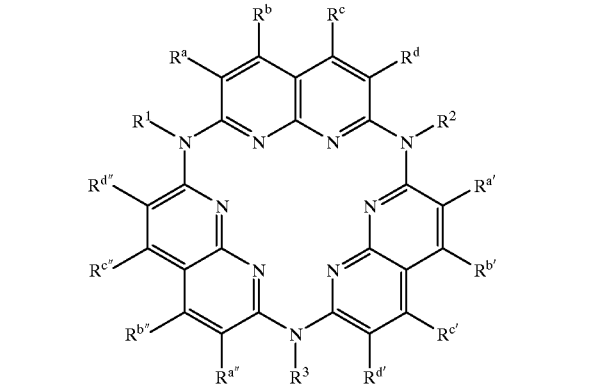

or a solvate, hydrate, ester or salt thereof; wherein:
  $R^1$, $R^2$ and $R^3$ are each independently selected from hydrogen, alkyl, cycloalkyl, aryl, aralkyl, heterocycle and formyl, any of which is optionally substituted;
  $R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each independently selected from hydrogen, alkyl, cycloalkyl, hydroxyalkyl, alkoxyalkyl, aryloxyalkyl, alkenyl, alkynyl, aryl, acyl, sulfonyl, alkylsulfonyl, arylsulfonyl, aminosulfonyl, nitroalkyl, aminoalkyl, monoalkylaminoalkyl, dialkylaminoalkyl, carboxy, amino, nitro, cyano, acyl, aminocarbonyl, hydroxy, alkoxy, aryloxy, aminocarbonyloxy, carbonylamino, sulfonylamino or aralkyl, any of which is optionally substituted, comprising:

(a) treating a compound of Formula II

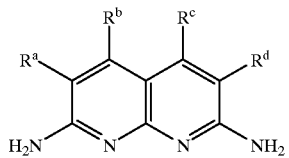

wherein $R^a$, $R^b$, $R^c$ and $R^d$ are as defined above, with hydrogen chloride gas.

11. A method for extracting a transition metal which comprises contacting a material containing the transition metal with a composition which comprises as an active extracting ingredient a compound of the following Formula:

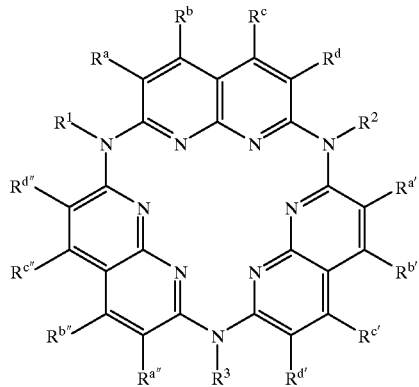

or a solvate, hydrate, ester or salt thereof; wherein:
$R^1$, $R^2$ and $R^3$ are each independently selected from hydrogen, alkyl, cycloalkyl, aryl, aralkyl, heterocycle and formyl, any of which is optionally substituted;
$R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each independently selected from hydrogen, alkyl, cycloalkyl, hydroxyalkyl, alkoxyalkyl, aryloxyalkyl, alkenyl, alkynyl, aryl, acyl, sulfonyl, alkylsulfonyl, arylsulfonyl, aminosulfonyl, nitroalkyl, aminoalkyl, monoalkylaminoalkyl, dialkylaminoalkyl, carboxy, amino, nitro, cyano, acyl, aminocarbonyl, hydroxy, alkoxy, aryloxy, aminocarbonyloxy, carbonylamino, sulfonylamino or aralkyl, any of which is optionally substituted, to extract the transition metal from the material.

12. A composition for extracting a transition metal which comprises a compound of the following Formula:

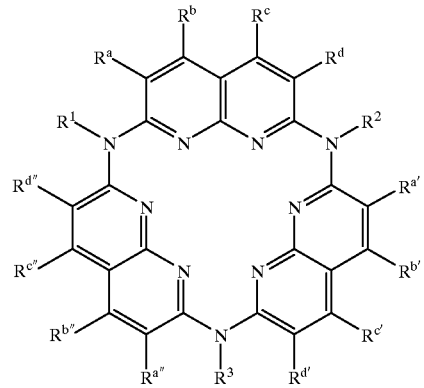

or a solvate, hydrate, ester or salt thereof; wherein:
$R^1$, $R^2$ and $R^3$ are each independently selected from hydrogen, alkyl, cycloalkyl, aryl, aralkyl, heterocycle and formyl, any of which is optionally substituted;
$R^a$, $R^{a'}$, $R^{a''}$, $R^b$, $R^{b'}$, $R^{b''}$, $R^c$, $R^{c'}$, $R^{c''}$, $R^d$, $R^{d'}$ and $R^{d''}$ are each independently selected from hydrogen, alkyl, cycloalkyl, hydroxyalkyl, alkoxyalkyl, aryloxyalkyl, alkenyl, alkynyl, aryl, acyl, sulfonyl, alkylsulfonyl, arylsulfonyl, aminosulfonyl, nitroalkyl, aminoalkyl, monoalkylaminoalkyl, dialkylamninoalkyl, carboxy, amino, nitro, cyano, acyl, aminocarbonyl, hydroxy, alkoxy, aryloxy, aminocarbonyloxy, carbonylamino, sulfonylamino or aralkyl, any of which is optionally substituted, and
an extraction accelerator selected from the group consisting of pyridine, methylpyridine, ethylpyridine, quinoline, tryptophan and phenylalanine.

* * * * *